United States Patent

Mizukami et al.

[11] Patent Number: 5,980,445
[45] Date of Patent: *Nov. 9, 1999

[54] PROCESS FOR PRODUCING DIARYL CARBONATE

[75] Inventors: Masamichi Mizukami; Yoshihisa Arai; Hidefumi Harada; Takuo Ohshida; Hiroaki Ohgi, all of Tsukuba, Japan

[73] Assignee: Mitsubishi Gas Chemical Company, Inc., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/965,617

[22] Filed: Nov. 6, 1997

[30] Foreign Application Priority Data

Nov. 22, 1996 [JP] Japan ..................................... 8-312013
Nov. 22, 1996 [JP] Japan ..................................... 8-312014

[51] Int. Cl.$^6$ ...................................................... C07C 69/96
[52] U.S. Cl. ............................................ 555/274; 558/277
[58] Field of Search ...................................... 558/274, 277

[56] References Cited

U.S. PATENT DOCUMENTS

| | | | |
|---|---|---|---|
| 5,166,393 | 11/1992 | Fukuoka et al. | 558/274 |
| 5,284,965 | 2/1994 | Buysch et al. | 558/270 |
| 5,344,954 | 9/1994 | Schon et al. | 558/274 |
| 5,565,603 | 10/1996 | Saleh et al. | 558/275 |

FOREIGN PATENT DOCUMENTS

| | | |
|---|---|---|
| 51-75044 | 6/1976 | Japan . |
| 51-105032 | 9/1976 | Japan . |
| 55-102542 | 8/1980 | Japan . |
| 55-102543 | 8/1980 | Japan . |
| 57-26645 | 2/1982 | Japan . |
| 8-119907 | 5/1996 | Japan . |

*Primary Examiner*—Johann Richter
*Assistant Examiner*—Joseph Murray
*Attorney, Agent, or Firm*—Sughrue, Mion, Zinn, Macpeak & Seas, PLLC

[57] ABSTRACT

A process for producing diaryl carbonate which comprises (A) a step for producing dialkyl carbonate represented by the general formula RO—CO—OR by reacting urea with alkyl alcohol represented by the general formula ROH, (B) a step for producing both alkyl aryl carbonate represented by the general formula RO—CO—OAr and diaryl carbonate represented by the general formula ArO—CO—OAr by reacting dialkyl carbonate produced in the above step (A) with an aromatic hydroxy compound represented by the general formula ArOH, and (C) a step for producing diaryl carbonate represented by the general formula ArO—CO—OAr by allowing to conduct disproportionation reaction of unreacted alkyl aryl carbonate produced in the above step (B), wherein R shows an alkyl group and Ar shows a non-substituted phenyl group or a phenyl group substituted by alkyl group, alkoxy group, aryl group, aryloxy group or halogen.

4 Claims, No Drawings

PROCESS FOR PRODUCING DIARYL CARBONATE

BACKGROUND OF THE INVENTION

1) Field of the Invention

The present invention relates to a process for producing diaryl carbonate, and specifically, to a process for producing diaryl carbonate using urea as raw material via dialkyl carbonate as intermediate product. Diaryl carbonate is a compound useful as a raw material for the production of polycarbonate according to a molten transesterification method.

2) Prior Art

Hitherto, diaryl carbonate has been produced by the reaction of an aromatic hydroxy compound with phosgene. However, a process for producing diaryl carbonate without using phosgene has been required since phosgene has high toxicity and high corrosion behavior for apparatus and furthermore a large amount of alkali is necessary to neutralize by-produced hydrogen chloride. Therefore, some processes for producing diaryl carbonate without using phosgene have been attempted.

For example, a process which comprises conducting carbonylation of an aromatic hydroxy compound with oxidation by using both carbon monoxide and oxygen has been suggested (Japanese Patent Kokai (Laid-open) No.53-68744). However, the process includes a very complicated reaction system since very expensive palladium is used as main catalyst and furthermore cocatalyst, drying agent, oxidizing agent, etc., also are required. Further, under the present situation, it is difficult to recover catalyst and the process does not reach to an industrial level also in respect of yield and reaction rate.

On the other hand, it has been attempted to produce diphenyl carbonate by direct reaction of urea with phenol, but its yield is low (Japanese Patent Kokai (Laid-open) No. 8-92167). Further, it is known to convert urea to diphenyl urea and further convert it into phenyl urethane and then allow to conduct disproportionation of phenyl urethane, but the operation is intricate (Japanese Patent Kokai (Laid-open) No. 8-198815).

As processes for producing diaryl carbonate other than the above-mentioned processes, Japanese Patent Kokai (Laid-open) No. 51-105032 discloses a process for producing diphenyl carbonate by the reaction of phenol with dimethyl carbonate under an atmospheric pressure or an applied pressure in the presence of a catalyst selected from the group consisting of Lewis acid and transition metal compounds capable of forming Lewis acid, but the selectivity to dephenyl carbonate is low.

Japanese Patent Kokai (laid-open) No. 51-75044 discloses a process for producing diphenyl carbonate by contacting phenyl methyl carbonate or phenyl ethyl carbonate with a catalyst composition selected from the group consisting of Lewis acid and transition metal compounds capable of forming Lewis acid, but the conversion rate of pheny methyl carbonate or pheny ethyl carbonate is low.

Further, in the production of diphenyl carbonate from dimethyl carbonate, separation between dimethyl carbonate and methanol has been become very problematic since dimethyl carbonate forms an azeotrope with methanol. In order to avoid such azeotropy, every endeavor has been made (Japanese Patent Kokai (Laid open) Nos. 54-48732, 61-291545 and 7-330687, etc.). However, the fundamental problem that reaction efficiency is inferior, has not yet been solved since dialkyl carbonate as the raw material is slipped out during the reaction.

As processes for synthesis of dialkyl carbonate, (1) an oxidative carbonylation process which comprises reacting alcohol with both carbon monoxide and oxygen (Japanese Patent Kokai (Laid-open) No. 51-138620), (2) a nitrite ester process which comprises reacting a nitrite ester with carbon monoxide (Japanese Patent Kokai (Laid-open) No. 3-141243), (3) an ethylene carbonate process which comprises allowing to conduct transesterification between ethylene carbonate and alkyl alcohol (Japanese Patent Kokai (Laid-open) No. 8-176071 and (4) a urea process which comprises reacting directly urea with alkyl alcohol (Japanese Patent Kokai (Laid-open) Nos. 55-102542 and 8-119907).

In above-mentioned (1) the oxidative carbonylation process and (2) the nitrite ester process, the reaction apparatus becomes complicated since toxic CO is used. (3) The ethylene carbonate process includes both a process using ethylene oxide and carbon dioxide and a process using urea and ethylene glycol, as the raw material of ethylene carbonate. The process using ethylene oxide as the raw material is not preferable since ethylene glycols are produced together. The process using urea as the raw material is more complicated than (4) the process for producing directly dialkyl carbonate from urea.

In a process described in Japanese Patent Kokai (Laid-open) No. 55-102542 corresponding to (4) the process which comprises reacting directly urea with alkyl alcohol, dialkyl carbonate is obtained by using a higher alcohol having 8 or above carbon atoms. Japanese Patent Kokai (Laid-open) No. 8-119907 discloses a process for producing dialkyl carbonate from methanol or ethanol, but its yield is very low.

Thus, under the present situation, no process in which diaryl carbonate can be produced in a high yield by simple operation without using toxic phosgene, has yet been established.

SUMMARY OF THE INVENTION

An object of the present invention, in order to solve above-mentioned problems, is to provide a process for producing diaryl carbonate in a high yield by simple operation without using toxic phosgene.

The inventors conducted an extensive study for solving the above-mentioned prior art problems. The inventors attempted a process which comprises reacting urea with alkyl alcohol to obtain dialkyl carbonate and then reacting dialkyl carbonate thus obtained with an aromatic hydroxy compound, thus producing diaryl carbonate. As a result, the inventors have found that alkyl aryl carbonate is obtained by the reaction of dialkyl carbonate obtained by the reaction between urea and alkyl alcohol with an aromatic hydroxy compound and diaryl carbonate can be obtained by further reaction of alkyl aryl carbonate thus obtained with an aromatic hydroxy compound, but diaryl carbonate cannot be obtained in a high yield since the reaction between alkyl aryl carbonate and the aromatic hydroxy compound proceeds only to some degree and then stops.

Therefore, as a result of further extensive study, the inventors have found that alkyl aryl carbonate is obtained as a reaction product between dialkyl carbonate and a hydroxy compound and then diaryl carbonate can be obtained in a high yield by allowing to conduct disproportionation reaction of unreacted alkyl aryl carbonate which does not yet react with the aromatic hydroxy compound, under a lower pressure than the reaction pressure in the reaction of dialkyl carbonate with the aromatic hydroxy compound while withdrawing dialkyl carbonate outside the reaction system, and accomplished the present invention.

Further, the inventors have found also that alcohol is readily separated by using an alkyl alcohol having 3 to 6 carbon atoms as raw material since the difference of boiling point between alcohol by-produced by the reaction of dialkyl carbonate with the aromatic hydroxy compound and dialkyl carbonate is properly present and alcohol is not substantially consumed since by-produced alcohol can be used again in the reaction with urea.

That is, the present invention provides a process for producing diaryl carbonate which comprises:

(A) a step for producing dialkyl carbonate represented by the following general formula (2) by reacting urea with alkyl alcohol represented by the following general formula (1), (B) a step for producing both alkyl aryl carbonate represented by the following general formula (4) and diaryl carbonate represented by the following general formula (5) by reacting dialkyl carbonate produced in the above step (A) with an aromatic hydroxy compound represented by the following general formula (3), and (C) a step for producing diaryl carbonate represented by the following general formula (5) by allowing to conduct disproportionation reaction of unreacted alkyl aryl carbonate produced in the above step (B);

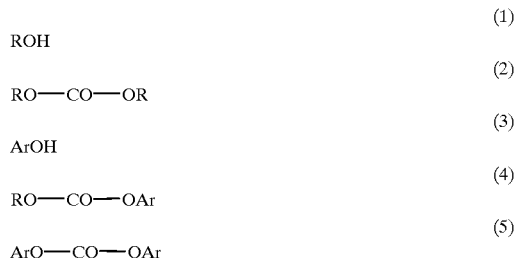

| | |
|---|---|
| ROH | (1) |
| RO—CO—OR | (2) |
| ArOH | (3) |
| RO—CO—OAr | (4) |
| ArO—CO—OAr | (5) | wherein R shows an alkyl group and Ar shows a non-substituted phenyl group or a phenyl group substituted by alkyl group, alkoxy group, aryl group, aryloxy group or halogen.

DETAILED DESCRIPTION OF THE INVENTION

The present invention will be described in detail below.

In the present invention, dialkyl carbonate as precursor is produced before diaryl carbonate is produced.

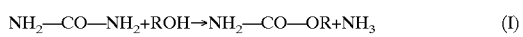

$$NH_2—CO—NH_2 + ROH \rightarrow NH_2—CO—OR + NH_3 \quad (I)$$

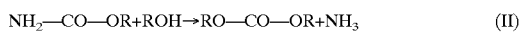

$$NH_2—CO—OR + ROH \rightarrow RO—CO—OR + NH_3 \quad (II)$$

In the reaction stage (I), urea reacts alkyl alcohol to produce alkyl carbamate and, in the reaction stage (II), alkyl carbamate thus produced reacts alkyl alcohol to produce dialkyl carbamate. Usually, the reaction to produce carbamate from urea is rapid and the reaction to produce carbonate from carbamate is slow. In each reaction stages (I) and (II), preferable reaction conditions are different from each other. Therefore, when the reactions (I) and (II) are continuously conducted, it is necessary to conduct each reaction by separating each into two stages. When the reactions (I) and (II) are conducted in batch wise, they may be conducted one by one in one and the same reactor.

In the reaction stage (I) wherein carbamate is produced from urea, it is possible to conduct the reaction at a comparatively low temperature since the reaction is rapid. It is preferable that the reaction temperature is 100 to 200° C. When the reaction temperature in the reaction stage (I) is too high, it is not preferable since side reactions occur.

The reaction pressure is preferably atmospheric pressure to 2 MPa. In the reaction system, a pressure control valve is provided since ammonia is produced, and the reaction is conducted while maintaining the interior pressure of the reaction system to a specified pressure and exhausting ammonia. In order to exhaust selectively only ammonia outside the reaction system, it is preferable to equip a distillation column at an upper portion of the reactor.

The reaction time is about 1 to 4 hours. The reaction may be conducted while flowing an inert gas such as nitrogen into the reaction system, though, usually, it is not necessary since the reaction is sufficiently rapid.

In the reaction stage (II) wherein carbonate is produced from carbamate, it is preferable that the reaction temperature is 180 to 260° C. since the reaction is comparatively slow.

The reaction pressure is preferably atmospheric pressure to 3 MPa. Also in the reaction system, a pressure control valve is provided since ammonia is produced and the reaction is conducted while maintaining the interior pressure of the reaction system to a specified pressure and exhausting ammonia. In order to exhaust selectively only ammonia outside the reaction system, it is preferable to equip a distillation column at an upper portion of the reactor.

The reaction time is about 1 to 20 hours. If necessary, the reaction may be conducted while flowing an inert gas such as nitrogen to promote removal of ammonia.

The above-mentioned reactions (I) and (II) may be conducted in one and the same reactor or in each separate reactors. In each cases, it is preferable to use same catalyst.

As the catalyst for the reactions (I) and (II), many catalysts have been described in Japanese Patent Kokai (Laid-open) No. 55-102542, 57-26645 and 57-175147, etc.. All of them can be used in the present invention. Among them, particularly, an oxide, an alkoxide, an aryloxide or an alkyl substituted metal oxide of a metal selected from the group consisting of zinc, copper, lead, tin and titanium, an adduct of said compound and other compound or a mixture containing at least one member selected from the foregoing compounds is preferably used. Examples of the catalyst include zinc oxide, diamyltin oxide, diamyltin diamyloxide, dibutyltin oxide, dibutyltin dibutoxide, tetraamyloxytin, tetrabutoxytin, tetraamyloxytitanium, tetrabutoxytitanium, etc, in which the above-mentioned compounds include all isomers thereof.

Alkyl alcohol of about 0.5 to 10 mole(s) to one mole of urea is used.

The amount of the catalyst is 0.1 to 20 mol % to urea. In the reactions (I) and (II), it is preferable that the alkyl alcohol is an alcohol having 3 or more carbon atoms. When carbon atom of the alkyl alcohol is 2 or below, it is not preferable since the yield is low and the pressure during the reaction is elevated.

After the completion of the reactions (I) and (II), unreacted alcohol, carbamate as intermediate product and catalyst are removed by distillation, thus obtaining dialkyl carbonate. Separated alcohol, cabamate and catalyst are recycled to use again.

Dialkyl carbonate thus obtained can be used in next reaction as it is. When it has not sufficient purity, it can be purified by crystallizing carbamate to separate and remove or by washing carbamate with warm water to remove. Further, After the washing, it is possible to purify further by distillation.

As a method for crystallization, it is possible to add a poor solvent such as hexane, heptane, octane, etc and then cool. According studies of the inventors, carbamate is sedimentated by cooling merely a mixture liquid of carbonate and carbamate, whereby pure carbonate can be obtained. It is preferable that the cooling temperature is −40° C. to a room temperature.

After carbamate has been sedimentated by cooling, pure dialkyl carbonate can be obtained by filtration of the liquid. The liquid for purification by cooling may be a reaction liquid itself or a distillate after a reaction liquid has been distilled. After the purification, it is preferable also to conduct again purification by distillation.

Methods for washing with warm water include a method wherein a mixture of carbonate and carbamate is contacted with warm water of 1 to 10 times by volume or a method wherein a mixture of carbonate and carbamate is dissolved in an organic solvent, e.g., toluene and then contacted with warm water. It is preferable that the temperature of warm water is 60 to 100 ° C. After the purification by washing, it is preferable also to conduct again purification by distillation..

Next, a process for producing diaryl carbonate by reacting dialkyl carbonate thus obtained with an aromatic hydroxy compound (ArOH) will be described below.

(III)

(IV)

In the reaction stage (III), dialkyl carbonate reacts an aromatic hydroxy compound to produce alkyl aryl carbonate (RO—CO—OAr). Then, in the reaction stage (IV), a portion of alkyl aryl carbonate thus produced further reacts an aromatic hydroxy compound to produce diaryl carbonate (ArO—CO—OAr). Both reactions are conducted while withdrawing alkyl alcohol since both reactions (III) and (IV) are an equilibrium reaction. The reaction conditions in both reactions need not be distinguished since both reactions proceed simultaneously.

Both reactions (III) and (IV) are conducted at a reaction temperature of 160 to 250° C. under a reaction pressure of 0.01 to 1 MPa. It is necessary to conduct both reactions while withdrawing alkyl alcohol in order to promote both reactions since both reactions are an equilibrium reaction. In order to withdraw selectively only alkyl alcohol outside the reaction system, it is preferable to equip a distillation column at an upper portion of the reactor.

The reaction time is about 1 to 10 hours. It is possible also to conduct both reactions while flowing an inert gas such as nitrogen into the reaction system, though, usually, it is not necessary. In both reaction, usually, a mixture of alkyl aryl carbonate and diaryl carbonate is produced.

It was found that the above reaction (IV) proceeded only to some degree and then stopped and thus diaryl carbonate could not be obtained in a high yield.

As a result of further studies of the inventors, it was found that diaryl carbonate could be obtained in a high yield by allowing to conduct disproportionation reaction of unreacted alkyl aryl carbonate which produced in the reaction (III) and does not yet react in the reaction (IV). That is, the following reaction (V), i.e., disproportionation reaction is allowed to conduct.

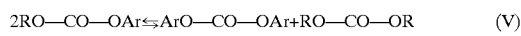

(V)

The above reaction (V) is an equilibrium reaction.

In the reaction stages (III) and (IV), the reactions (III) and (IV) are conducted while withdrawing alkyl alcohol. In the reaction stage (V) of disproportionation, the reaction (V) is conducted while withdrawing dialkyl carbonate. Thus, preferable reaction conditions are different between the reaction stages (III) and (IV) and the reaction stage (V). When the reactions (III), (IV) and (V) are continuously conducted, it is necessary to separate the reactions into two stages. When the reactions (III), (IV) and (V) are conducted in batch wise, they may be conducted one by one in one and the same reactor.

In the reaction stage (III) wherein alkyl aryl carbonate is produced, dialkyl carbonate is reacted until conversion rate of dialkyl carbonate comes to be about 20 to 60 % and then alkyl alcohol is removed to recycle and alkyl aryl carbonate thus produced is used as the raw material in the next reaction stage (V). Alkyl aryl carbonate produced in the reaction (III) further reacts with an aromatic hydroxy compound to produce a small amount of diaryl carbonate in the reaction (IV). The next disproportionation reaction (V) may be conducted without separating alkyl aryl carbonate thus produced in the reaction (IV). Alkyl alcohol obtained in the reaction stages (III) and (IV) is recycled to use again as the raw material in the reaction stages (I) and (II).

In the reaction stage (V) wherein diaryl carbonate is produced, the reaction temperature is 160 to 250° C. It is preferable that the reaction pressure in the reaction (V) is lower than that in the reactions (III) and (IV). The reaction pressure is 0.001 to 0.1 MPa and, preferably, 0.01 to 0.05 MPa. It is necessary to conduct the reaction (V) while withdrawing dialkyl carbonate in order to promote the reaction (V) since the reaction (V) is an equilibrium reaction. In order to withdraw selectively only dialkyl carbonate outside the reaction system, it is preferable to equip a distillation column at an upper portion of the reactor.

The reaction time is about 1 to 10 hours. It is possible also to conduct the reaction (V) while flowing an inert gas such as nitrogen into the reaction system, though, usually, it is not necessary. The reaction (V) is conducted until conversion rate of alkyl aryl carbonate comes to be about 80 to 100% and then unreacted alkyl aryl carbonate and catalyst are removed by distillation, thus obtaining diaryl carbonate.

The reactions (III), (IV) and (V) may be conducted in one and the same reactor or in each separate reactors. In all cases, it is preferable to use same catalyst.

The catalyst to be used in the reactions (III), (IV) and (V) is not limited on condition that it is known usually as a transesterification catalyst. Particularly, an oxide, an alkoxide, an aryloxide, an alkyl substituted metal oxide or an acetylacetonate of a metal selected from the group consisting of titanium, aluminum, gallium, tin and yttrium or an adduct of said compound and other compound are preferably used.

Among the above-mentioned catalyst, particularly, titanium compounds represented by the general formula $Ti(OX)_4$ wherein X shows an alkyl group having 3 to 6 carbon atoms or an aryl group, an adduct of titanium compound represented by the general formula $Ti(OX)_4$. XOH wherein X shows an alkyl group having 3 to 6 carbon atoms or an aryl group, are preferably used.

Examples of the catalyst represented by the above-mentioned general formulas include titanium tetra propoxide including each isomers thereof, titanium tetrabutoxide including each isomers thereof, titanium tetraamyloxide including each isomers thereof, titanium tetrahexyloxide including each isomers thereof, titanium tetrapheoxide, titanium tetra(4-methylpheoxide), an adduct of titanium tetraphenoxide and phenol, etc.

Further, it is preferable also to use tin compounds represented by the general formulas $R'_2SnO$, $R'_2Sn(OR'')_2$ and $Sn(OR)_4$ wherein R' shows an alkyl group having 1 to 10 carbon atoms and R" shows an alkyl group having 3 to 6 carbon atoms.

Examples of the catalyst represented by the above-mentioned general formulas include diethyltin oxide, dipropyltin oxide including each isomers thereof, dibutyltin oxide including each isomers thereof, diamyltin oxide including each isomers thereof, dioctyltin oxide including each isomers thereof, dibutyldibutoxytin including each isomers thereof, diethyldiamyloxytin including each isomers thereof, tetrabutoxytin including each isomers thereof, tetraisoamyloxytin including each isomers thereof, etc. Further, compounds to be changed to said compounds under the reaction condition, trialkylmonoalkoxide and monoalkyltrialkoxide also are suitably used.

In the reaction (III), the aromatic hydroxy compound of 0.2 to 10 times by mol and preferably 1 to 5 times by mol to dialkyl carbonate is used.

It is preferable that the amount of catalyst is 0.01 to 10 mol % to dialkyl carbonate. In the reaction (V), the reaction liquid of (III) is usually used as the raw material as it is. If necessary, a catalyst may be added.

According to the process of the present invention, alkyl alcohol by-produced by the reaction of dialkyl carbonate with an aromatic hydroxy compound reacts urea to be converted again into dialkyl carbonate. Therefore, alkyl alcohol can be recycled to use again. This is attained only by the proceeding of each reactions in a sufficiently high yield. When alkyl alcohol has 3 to 6 carbon atoms, it can be easily attained.

That is, it is preferable that dialkyl carbonate in the reaction (III) is one produced from alcohol having 3 to 6 carbon atoms. When its carbon atom is 2 or below, it is difficult to remove selectively only alcohol in the reaction stage (III) since the difference of boiling point between alcohol and dialkyl carbonate is small. When its carbon atom is 7 or above, it is difficult to separate pure diaryl carbonate by distillation since the boiling point of diaryl carbonate as the product is close to that of alkyl aryl carbonate as the raw material. Further, in order to withdraw alkyl alcohol (ROH), it is necessary that the boiling point of aromatic hydroxy compound (ArOH) is higher than that of ROH. When its carbon atom is 7 or above, it is difficult to withdraw selectively ROH since the boiling point of ROH becomes close to that of ArOH.

The advantages to be provided by the use of alcohol having 3 to 6 carbon atoms will be summarized below.

In the step of producing diaryl carbonate from dialkyl carbonate, the separation between alcohol and dialkyl carbonate becomes easy since the difference of boiling point between alcohol and dialkyl carbonate is made large by using alcohol having 3 or above carbon atoms. Thereby, the problem that it is difficult to separate methanol from dimethyl carbonate can be solved.

The reaction is conducted efficiently since exhaustion of dialkyl carbonate accompanied by alcohol outside the reaction system during the reaction is suppressed. When alcohol having 7 or above carbon atoms is used, it is not preferable since boiling point of alcohol is equivalent to that of the aromatic hydroxy compound to be interchanged or higher than that and furthermore the separation between diaryl carbonate as the product and alkyl aryl carbonate as intermediate product becomes difficult. Generally, dialkyl carbonate formed of alcohol having 3 to 6 carbon atoms is not readily available.

When alcohol having 3 or above carbon atoms is used, the above-mentioned problem can be solved by recycling alcohol to form again carbonate since alcohol having 3 or above carbon atoms reacts directly urea to provide carbonate in a high yield. That is, in order to promote all the reactions in a high yield, it is indispensable to use alcohol having 3 to 6 carbon atoms.

Examples of alcohol having 3 to 6 carbon atoms to be used in the present invention include n-propanol, isopropanol, n-butanol, isobutanol, sec-butanol, tert-butanol, 1-pentanol, 2-pentanol, 3-pentanol, 2-methyl-1-butanol, 2-methyl-2-butanol, 3-methyl-1-butanol, 3-methyl-2-butanol, 2,2-dimethyl-1-propanol, cyclopentanol, 1-hexanol, 2-hexanol, 3-hexanol, 2-methyl-1-pentanol, 3-methyl-1-pentanol, 4-methyl-1-pentanol, 2,2-dimethyl-1-butanol, 2,3-dimethyl-1-butanol, 3,3-dimethyl-1-butanol, 2-ethyl-1-butanol and 3-ethyl-1-butanol.

The aromatic hydroxy compound represented by the general formula (3) to be used in the present invention is phenol or alkyl group-, alkoxy group-, aryl group-, aryloxy group- or halogen-substituted phenol. Examples of the aromatic hydroxy compound include phenol, o-cresol, m-cresol, p-cresol, 2,4-dimethylphenol, 3,4-dimethylphenol, 3,5-dimethylphenol, o-ethylphenol, m-ethylphenol, p-ethylphenol, p-n-propylphenol, p-isopropylphenol, p-n-butylphenol, p-isobutylphenol, p-tert-butylphenol, p-phenylphenol, p-methoxyphenol, p-phenoxyphenol, p-chlorophenol, 2,4-dichlorophenol, etc.

In carrying out the process of the present invention, it is possible to conduct the reactions using a solvent inert to the reactions, or in the presence of an inert gas or under an applied pressure with an inert gas. It is naturally preferable that each raw materials to be used in the present invention is pure. It is preferable that they have a purity 95 to 100%. Further, it is preferable that dialkyl carbonate as the intermediate product has a purity of 90 to 100%.

PREFERRED EMBODIMENT OF THE INVENTION.

Some of the preferred Embodiments of the present invention will be described in detail below, referring to Examples, which are not intended to limit the scope of the present invention.

In Examples, the term "pre-stage reaction" means reactions for producing dialkyl carbonate from urea and the term "post-stage reaction" means reactions for producing alkyl aryl carbonate and diaryl carbonate from dialkyl carbonate.

EXAMPLE 1

(Synthesis of diisoamyl carbonate)

A filling column of inner diameter 34 mm and length 500 mm was attached to an autoclave of capacity 3L, made by SUS316, equipped with a stirrer, thus preparing a reactor. A pressure control valve was provided to an end of the filling column so as to be able to maintain the interior pressure of the reactor to a specified pressure. Further, the filling column was filled with Dixon packing 212.8 g of (3.54 mol) of urea, 810.8 g (9.20 mol) of isoamyl alcohol and 10.7 g (0.13 mol) of zinc oxide were charged into the reactor. The interior space of the reactor was replaced with nitrogen, and then the interior temperature of the reactor was elevated to 180° C. over 1 hour and the state was maintained for further 1 hour at 180° C. Although the interior pressure of the reactor was increased due to generation of ammonia during the reaction, the interior pressure was maintained to 0.4 MPa (gauge) by exhausting ammonia outside the reactor via the pressure control valve. At this time, urea was mostly converted into carbamate and generation of ammonia became gradual.

Then, the temperature was elevated up to 250° C. over 8 hours and the pressure was adjusted so as to be 0.4 to 0.5 MPa (gauge), thus conducting the reaction. After the completion of the reaction, 186.1 g of excess isoamyl alcohol was removed by distillation and then a mixture of diisoamyl carbonate and isoamyl carbamate was obtained by distillation. The liquid contained 91% of diisoamyl carbonate. The crude diisoamyl carbonate was standing at 0° C for 12 hours and then crystallized carbamate was removed by filtration, thus obtaining 98% of diisoamyl carbonate. The yield of diisoamyl carbonate was 467.2 g (2.31 mol).

(Synthesis of diphenyl carbonate)

A filling column of inner diameter 50 mm and length 500 mm filled with Dixon packing was attached to a flask of capacity 2L, thus preparing a reactor. 467.2 g (2.31 mol) of diisoamyl carbonate thus obtained, 439.7 g (4.67 mol) of phenol and 9.71 g of (0.023 mol) of titanium tetraphenoxide were charged into the reactor and then heated in an oil bath of bath temperature 220° C. for 4 hours with stirring. The temperature of the reaction liquid was elevated from initial 180 ° C. to final 210° C . Further, meantime, the pressure was reduced from 760 mmHg to 460 mmHg at the reducing rate of about 75 mmHg/one hour to conduct the reaction while distilling off isoamyl alcohol (the amount distilled off: 86.4 g).

Then, the pressure was reduced to 100 mmHg to conduct disproportionation reaction of isoamyl phenyl carbonate for 2 hours while distilling off both phenol and diisoamyl carbonate. After the completion of the reaction for 6 hours as total, diphenyl carbonate was isolated by distillation. The yield of diphenyl carbonate was 93.0 g (0.4341 mol). The conversion rate of isoamyl phenyl carbonate was 84.1%. The amount of liquid distilled off during the reactions was 657.2 g as whole, which was composed of 325.4 g (3.46 mol) of phenol and 331.8 g (1.64 mol) of diisoamyl carbonate.

(Recycling of isoamyl alcohol)

810.8 g of isoamyl alcohol wherein 538.3 g of new isoamyl alcohol was added to 272.5 g of isoamyl alcohol recovered in both pre-stage reaction and post-stage reaction, was used to conduct again pre-stage reaction. No change of yield was observed.

EXAMPLE 2

(Synthesis of diisoamyl carbonate)

659 g of crude diisoamyl carbonate having a purity of 91% was synthesized in the same manner as in Example 1. The crude diisoamyl carbonate was contacted with 10 times by volume of warm water of 80° C. and washed by separation of liquid. The washing was repeated three times. The purity became 95% in first washing 97% in second washing: 98% in third washing. 4Diisoamyl carbonate thus obtained was again distilled to use as the raw material of next reaction. The yield of diisoamyl carbonate was 595 g.

(Synthesis of diphenyl carbonate)

Diphenyl carbonate was synthesized in the same manner as in Example 1 except that 467.2 g of diisoamyl carbonate washed with warm water was used. The yield of diphenyl carbonate was 83.1 g (0.388 mol). The conversion rate of isoamyl phenyl carbonate was 81.5%.

(Recycling of isoamyl alcohol)

810.8 g isoamyl alcohol wherein 530.5 g of new isoamyl alcohol was added to 186.1 g of isoamyl alcohol recovered in pre-stage reaction and 94.2 g of isoamyl alcohol recovered in post-stage reaction, was used to conduct again pre-stage reaction. No change of yield was observed.

EXAMPLE 3

94.8 g (1.58 mol) of urea, 1392 g (15.8 mol) of isoamyl alcohol and 14.5 g (0.058 mol) of di-n-butyltin oxide were charged to the same reactor as in Example 1. The interior space of the reactor was replaced with nitrogen and then the interior temperature of the reactor was elevated to 180° C. over 1 hour and the state was maintained for further 1 hour at 180 ° C. Although the interior pressure of the reactor was increased due to generation of ammonia during the reaction the interior pressure was maintained to 0.4 MPa (gauge) by exhausting ammonia outside the reactor via the pressure control valve. At this time, urea was mostly converted into carbamate and generation of ammonia became gradual.

Then, the temperature was elevated up to 230° C. over 3 hours and the pressure was adjusted so as to be 0.6 to 0.9 MPa (gauge), thus conducting the reaction.

Then, the reaction was further conducted at a reaction temperature of 230° C. under a pressure of 0.9 MPa for 3 hours. After the completion of the reaction, 1058 g of excess isoamyl alcohol was removed by distillation and then a mixture of diisoamyl carbonate and isoamyl carbamate was obtained by distillation. The liquid contained 96% of diisoamyl carbonate. Thus, it was used as it is. The yield of diisoamyl carbonate was 296 g (1.48 mol).

(Synthesis of diphenyl carbonate)

290.0 g (1.43 mol) of diisoamyl carbonate thus obtained, 272.9 g (2.90 mol) of phenol and 6.03 g (0.014 mol) of titanium tetrapheoxide were charged into the same reactor as in Example 1 and the same reaction as in Example 1 was conducted. The yield of diphenyl carbonate was 52.8 g (0.247 mol). The amount of recovered isoamyl alcohol was 56 g. The conversion rate of isoamyl phenyl carbonate was 80.2%.

(Recycling of isoamyl alcohol)

1392 g of isoamyl alcohol wherein 278 g of new isoamyl alcohol was added to 1114 g of isoamyl alcohol recovered in both pre-stage reaction and post-stage reaction, was used to conduct again pre-stage reaction. No change of yield was observed.

EXAMPLE 4

(Synthesis of di-n-butyl carbonate)

212.8 g (3.54 mol) of urea, 681.9 g (9.20 mol) of n-butyl alcohol and 10.7 g (0.13 mol) of zinc oxide were charged into the same reactor as in Example 1. The interior space of the reactor were replaced with nitrogen and then the interior temperature of the reactor was elevated to 180° C. over 1 hour and the state was maintained for further 1 hour at 180° C. Although the interior pressure of the reactor was increased due to generation of ammonia during the reaction, the interior pressure was maintained to 0.5 MPa (gauge) by exhausting ammonia outside the reactor via the pressure control valve. At this time, urea was mostly converted into carbamate and generation of ammonia became gradual.

Then, the temperature was elevated up to 250° C. over 8 hours and the pressure was adjusted so as to be 0.8 to 1.0 MPa (gauge), thus conducting the reaction. After the completion of the reaction, 156.6 g of excess n-butyl alcohol was removed by distillation and then a mixture of di-n-butyl carbonate and n-butyl carbamate was obtained by distillation. The liquid contained 80% of di-n-butyl carbonate. The reaction liquid was standing at 0° C. for 12 hours and then filtered, thus obtaining di-n-butyl carbonate having a purity of 97%. The yield of di-n-butyl carbonate was 259 g (1.50 mol).

(Synthesis of diphenyl carbonate)

A filling column of inner diameter 22 mm and length 200 mm filled with Dixon packing was attached to a flask of capacity 300 ml, thus preparing a reactor. 100 g (0.574 mol) of di-n-butyl carbonate thus obtained, 108 g (1.15 mol) of phenol and 1.43 g of (0.006 mol) of di-n-butyltin oxide were charged into the reactor and then heated in an oil bath of bath temperature 215° C. for 4 hours with stirring. The temperature of the reaction liquid was elevated from initial 180° C. to final 200° C. Further, meantime the pressure was atmospheric pressure to conduct the reaction while distilling off n-butyl alcohol (the amount distilled off: 16.6 g).

Then, the pressure was reduced to 125 mmHg to conduct disproportionation reaction of di-n-butyl carbonate for 2 hours while distilling off both phenol and di-n-butyl carbonate. After the completion of the reaction for 6 hours as total, diphenyl carbonate was isolated by distillation. The yield of diphenyl carbonate was 24.9 g (0.116 mol). The conversion rate of n-butyl phenyl carbonate was 83.2%.

(Recycling of n-butyl alcohol)

681.9 g of n-butyl alcohol wherein 508.7 g of new n-butyl alcohol was added to 173.2 g of n-butyl alcohol recovered in both pre-stage reaction and post-stage reaction, was used to conduct again pre-stage reaction. No change of yield was observed.

What is claimed is:

1. A process for producing diaryl carbonate which comprises (A) a step for producing diallyl carbonate represented by the following general formula (2) by reacting urea with an alkyl alcohol represented by the following general formula (1) in the presence of at least one catalyst selected from the group consisting of R'$_2$SnO, R'$_2$Sn(OR")$_2$ and Sn(OR)$_4$ wherein R' is an alkyl group having 1 to 10 carbon atoms and R" is an alkyl group having 3 to 6 carbon atoms, and then purifying the dialkyl carbonate obtained by distillation, either by cooling to −40 to 20° C. or by contacting with water having a temperature of 60 to 100° C.

(B) a step for producing both alkyl aryl carbonate represented by the following general formula (4) and diaryl carbonate represented by the following general formula (5) by reacting purified dialkyl carbonate produced in step (A) with an aromatic hydroxy compound represented by the following general formula (3), and by-produced alkyl alcohol represented by the general formula (1) is recycled for use as raw material in step (A), and (C) a step for producing diaryl carbonate represented by the following general formula (5) by allowing a disproportionation reaction of unreacted alkyl aryl carbonate produced in step (B) to occur under a lower reaction pressure than that of step (3);

ROH      (1)

RO—CO—OR      (2)

ArOH      (3)

RO—CO—OAr      (4)

ArO—CO—Oar      (5)

wherein R is an alkyl group having 3 to 6 carbon atoms and Ar is a non-substituted phenyl group or a phenyl group substituted by an alkyl group, an alkoxy group, an aryl group, an aryloxy group or a halogen atom.

2. A process for producing diaryl carbonate according to claim 1, wherein a catalyst is used in steps (B) and (C) said catalyst being an oxide, an alkoxide, an aryloxide or an alkyl substituted metal oxide of a metal selected from the group consisting of tin and titanium, an adduct of said compound or a mixture containing at least one member selected from the foregoing compounds.

3. A process for producing diaryl carbonate according to claim 2, wherein said catalyst used in steps (B) and (C) is Ti(OX)$_4$, R'$_2$SnO, R'$_2$Sn(OR')$_2$, Sn(OR)$_4$, an adduct of said compound and other compound or a mixture containing at least one member selected from the foregoing compounds in which X is an alkyl group having 3 to 6 carbon atoms or an aryl group; R' is an alkyl group having 1 to 10 carbon atoms and R" is an alkyl group having 3 to 6 carbon atoms.

4. A process for producing diaryl carbonate according to claim 1, wherein said Ar is phenyl group.

* * * * *